United States Patent [19]
Anderson

[11] Patent Number: 5,919,194
[45] Date of Patent: Jul. 6, 1999

[54] ORTHOPAEDIC IMPLANT

[76] Inventor: David L. Anderson, 609 East Sunset North, Redlands, Calif. 92373

[21] Appl. No.: 08/897,519

[22] Filed: Jul. 21, 1997

[51] Int. Cl.[6] .................................................. A61B 17/68
[52] U.S. Cl. .............................................. 606/72; 606/60
[58] Field of Search ................................ 606/72, 73, 60, 606/61, 62, 63, 67, 68

[56] References Cited

U.S. PATENT DOCUMENTS

| | | | |
|---|---|---|---|
| 2,562,419 | 4/1951 | Ferris | 606/72 |
| 2,760,488 | 8/1956 | Pierce | 606/72 |
| 3,489,143 | 1/1970 | Halloran | 606/72 |
| 5,098,433 | 3/1992 | Freedland | 606/63 |
| 5,464,427 | 11/1995 | Curtis et al. | 606/72 |

*Primary Examiner*—Guy V. Tucker
*Attorney, Agent, or Firm*—Lyon & Lyon LLP

[57] ABSTRACT

An orthopaedic implant, namely a locking device for anchoring to cortical bone for the fixation of fractures of bone and/or dislocations of joints. The locking device includes a cable, a locking member slidable over the cable, and a spreader member attached to a distal end of the cable. The locking member has an expandable portion that may be expanded when the locking member engages the spreader member. A capturing assembly has a raised portion and a contractible passage therethrough for securably receiving a proximal portion of the cable, and preferably includes a cooperating sleeve and annular-shaped member adapted to contract the contractible passage. The cable and locking device are introduced through a hole in a bone, the locking member is expanded, thereby engaging the distal or far surface of the bone. The capturing assembly is introduced over the cable until the raised portion engages the proximal or near surface of the bone. Tension is applied to the cable, and the annular-shaped member is directed into the sleeve, thereby contracting the contractible passage and securing the cable therein.

16 Claims, 4 Drawing Sheets

ORTHOPAEDIC IMPLANT

FIELD OF THE INVENTION

The present invention relates generally to orthopaedic surgical devices, and more particularly to a device for securing bone segments against one another, such as for fixing bone fractures and joint dislocations.

BACKGROUND OF THE INVENTION

Various types of orthopaedic devices have been described for the fixation of bone fragments. Such devices are often used to stabilize bones, thereby enhancing the healing of fractures and/or promoting union of joints being fused together. This stability helps allow early return of the function of the body part and improves patient well being.

For example, bone screws are commonly used devices for fixing bone fragments. The bone fragments are positioned in their proper configuration, and one or more holes are then drilled and tapped across the fracture. The screws are then screwed into the holes, thereby compressing the bone fragments, for example, by using a lag screw technique of over-drilling a gliding hole in the near side (cortex) of the bone. In addition, bone screws are often used in conjunction with metal plates to increase stability against multiplanar forces which may act upon the bone fragments. The screws are placed through holes in the plates, thereby lagging the plate against the bone in compression.

Metal pins (e.g. Kirschner wires and Steinman pins) are also often used to stabilize bones. The pins may be threaded or smooth, and are drilled across bone fragments to provide stability to the bone. Pins may also be used together with external fixators to gain purchase of bone fragments. These devices include an external rigid framework that lies outside of the body. Pins are inserted through the framework and into the body, by piercing the skin and inserting the pins into drilled, tapped holes in the bone.

Intramedullary implants are another conventional device used, especially for long, tubular bone fragments. These nail-like devices are placed in the central canal of a bone to gain an interference fit and/or are locked at the ends by screws to secure the bone fragments in place. Such implants act as an internal splint within the bone, and allow compression of the bone piece during weight bearing.

Cables are also used to hold bone pieces together, for example by wrapping a cable around long, thin pieces of bone and then tensioning the cable, the bone fragments may be held together. The cables are typically held by a metal crimping piece that maintains the tension of the cable. Wrapping the cable around bone pieces in a cerlage technique is limited, however, and is generally used only to fix cracks in only one cortex of a tubular bone, or to link long slabs of bone (known as cortical struts) onto the outer surface of a tubular bone. In particular, very oblique or long spiral fractures in long tubular bones may be secured by cables to hold the bone in a stable state of compression.

Other bone anchors have been used primarily to attach suture materials to bone so that the suture may be secured to soft tissue, such as a ligament or tendon, thereby tightly linking the tissue to the bone. These devices typically anchor themselves in a hole drilled into the bone, thus preventing the device from pulling away from the bone as tension is applied to the attached soft tissue structure.

These conventional bone fixation devices generally gain their purchase to the bone by engaging the interior of the bone, i.e., the cancellous bone material. Cancellous bone is soft and spongy in nature and consequently has inferior holding power as compared with the exterior portion of the bone, i.e. cortical bone. The tension imposed on the devices after implantation may exceed the stresses that the bone-implant interface is able to resist, and may result in implant failure. Such devices may also require extensive surgical exposure of the bones to allow implantation of the devices, which may result in increased risk of infection and/or increased pain in the patient.

In contrast, external fixator devices may not require extensive surgical exposure, because they merely violate the skin with pins. However, use of such devices may be complicated by infection in and around the pin tracts beneath the skin. These external devices may also reduce patient comfort as compared to internally implanted devices.

Finally, although cable devices provide excellent tensionresistance, their use is generally limited because of the limited methods of attaching the cable to bone.

Accordingly, there is a need for an improved orthopaedic implant device that provides increased bone purchase and/or may be implanted with minimal surgical exposure.

SUMMARY OF THE INVENTION

In accordance with the present invention, an orthopaedic implant or locking device is disclosed for compressibly securing a hard tissue structure, such as a bone having a fracture therein. The locking device includes an elongate member, preferably a cable or metal rod, having proximal and distal ends, and having a proximal portion.

A locking member is slidably received over the cable, and has a radially expandable portion capable of being expanded between contracted and enlarged conditions, and preferably comprising a plurality of flanges disposed radially about the locking member. The radially expandable portion includes a proximal surface for engaging a far or distal surface of the bone.

A retaining or spreader member is attached or integrally formed on the distal end of the cable. The spreader member is adapted to be slidably engaged by the locking member to prevent the locking member from sliding distally off the cable. Preferably, the spreader member has a tapered portion extending proximally from the distal end of the cable, more preferably having a frustoconical shape, for expanding the radially expandable portion of the locking member.

The locking device also includes a capturing assembly having a contractible passage therein for securably receiving the proximal portion of the cable therethrough. The capturing assembly includes a raised portion, preferably an annular flange, having a distal surface for engaging the near or proximal surface of the bone being stabilized by the device.

Preferably, the capturing assembly includes a capturing sleeve having the raised portion extending radially about the sleeve, and having an aperture therein at least partially defined by a flange. The flange also partially defines the contractible passage extending through the capturing sleeve. In addition, the capturing assembly preferably also includes an annular-shaped threaded member adapted to be rotatably received within the aperture in the capturing sleeve. As the threaded member is screwed into the aperture, it forces the flange radially inward, thereby contracting the contractible passage to secure the cable inserted therethrough.

To implant the locking device in accordance with the present invention, a bone is positioned in a desired configuration, and a hole is drilled from a proximal portion to a distal portion of the bone, preferably from the anterior surface to the posterior surface thereof, for example across a fracture being stabilized therein. The distal end of the cable with the locking member thereon is introduced into the hole until it is at least partially exposed beyond the far or distal surface of the bone.

The radially expandable portion of the locking member is expanded to its enlarged condition, thereby having a cross-section substantially larger than the hole, and being able to substantially engage the far or distal surface of the bone and prevent the distal end of the cable from moving proximally. The capturing assembly is then directed over the proximal end of the cable until it engages the near or proximal surface of the bone.

A predetermined tension is applied to the proximal end of the cable, and the capturing assembly is contracted to secure the cable therein. For example, the threaded member may be screwed or otherwise directed into the capturing sleeve, thereby forcing the flange on the capturing sleeve to contract the contractible passage and substantially secure the cable therein. The tension is then released from the proximal end of the cable, thereby compressing the bone between the proximal and distal portions thereof and consequently securing the fracture therein. In this embodiment, the cable may be substituted by a metal rod serving a similar although more rigid function of maintaining tension between the distal locking member of the proximal capturing assembly.

In a second preferred embodiment, the locking device includes a pair of cables, each having a spreader member and a locking member thereon. The cables are preferably used to stabilize two separate bone fragments disposed adjacent one another. A hole is drilled into each bone, each cable is introduced into the respective hole, and each locking members is expanded to engage the far or distal surface of the respective bone. A centering sleeve having a raised portion thereon is then directed over each cable until it abuts the near or proximal surface of each bone fragment.

A crimper member is then provided having a pair of passages therein for receiving the cables therethrough. A predetermined tension may be applied to each cable, and then the crimper member may be crushed or compressed, thereby securing the cables therein.

Orthopaedic implant devices in accordance with the present invention provide a compressive locking device for stabilizing a bone structure having a fracture therein or being fused after a joint dislocation. The compressive forces imposed by the locking device are applied to the outer surfaces of the bone structure, that is, cortical bone rather than cancellous bone. Thus, the locking device may provide substantially greater stress resistance than devices which screw into soft cancellous bone. Further, a locking device in accordance with the present invention may require only a limited surgical exposure, thereby enhancing patient comfort and minimizing risk of infection.

Thus, it is an object of the present invention to provide an improved orthopaedic implant for securely fixing bone segments together, thereby facilitating healing and comfort of the patient.

Additional objects and features of the present invention will become apparent from consideration of the following description taken in conjunction with the accompanying drawings.

DETAILED DESCRIPTION OF THE PREFERRED EMBODIMENT

Figure 1:
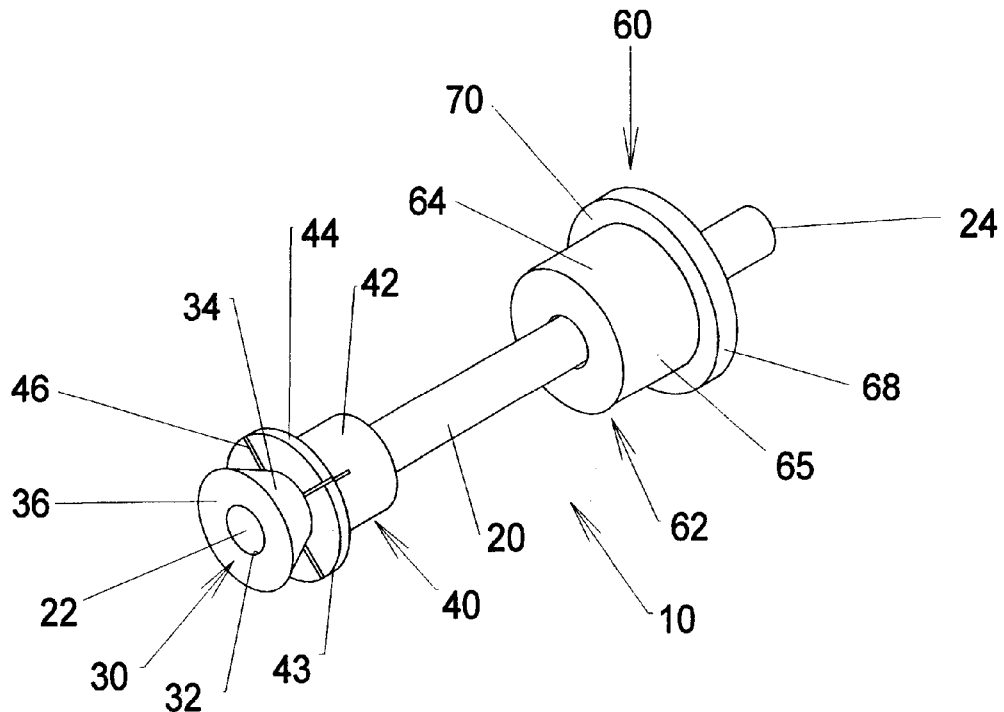
FIG. 1 is a perspective view of a first preferred embodiment of a locking device in accordance with the present invention with a locking member in its contracted condition prior to deployment.
Figure 2:
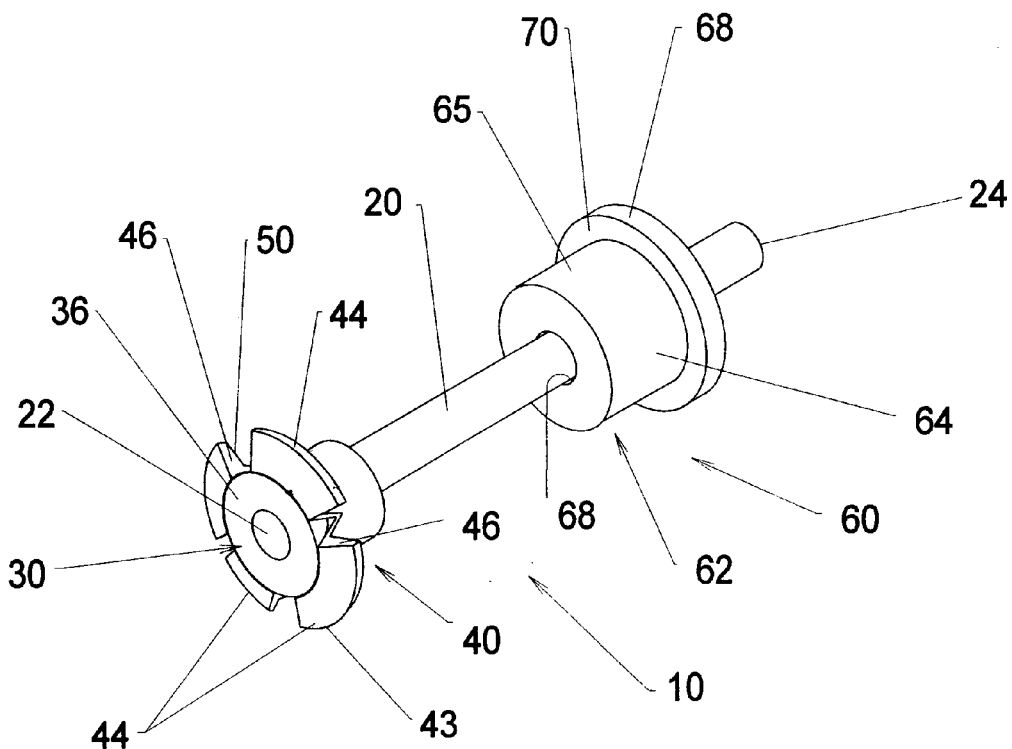
FIG. 2 is a perspective view of the locking device of FIG. 1 with the locking member in its enlarged condition after deployment.

Turning to FIGS. 1–3, 5A and 5B, a preferred embodiment of an orthopaedic implant device in accordance with the present invention is shown, namely a locking device 10. The locking device 10 includes a cable 20, a spreader member 30, a locking member 40, and a capturing assembly 60. The cable 20 comprises an inelastic elongate member having a distal end 22 and a proximal end 24. The spreader member 30 is a retaining member that is substantially permanently attached to the distal end 22 of the cable 20. Preferably, the spreader member 30 includes a passage 32 into which the distal end 22 of the cable 20 is inserted and affixed, for example, by adhesives, welding, crimping and the like. Alternatively, the spreader member 30 may be integrally formed on the cable 20 or may abut and extend distally from the distal end 22.

The spreader member 30 includes a distal base 36 and tapers towards the proximal end 24 of cable 20, providing a tapered proximal surface 34 for engaging the locking member 40. Preferably, the spreader member 30 has a conical or frustoconical shape that tapers proximally from the distal end 22 of the cable 20 along a portion thereof. Alternatively, the spreader member 30 may include other configurations or segments, for example, one or more radially extending flanges or tabs to prevent the locking member 40 from sliding distally off of the cable 20 and/or a ramped proximal portion for expanding the locking member 40.

The locking member 40 comprises a substantially cylindrical member having a passage 48 (FIG. 3) extending axially therethrough, and having an expandable portion 43 capable of being radially expanded from an initial contracted condition to an enlarged condition. Preferably, the locking member 40 includes a cylindrical sleeve 42 having a plurality of flanges or fins 44 extending radially therefrom. More preferably, the locking member 40 has four fins 44 integrally formed thereon having a proximal surface 50, and together defining a substantially annular shape. The fins 44 are separated by notches or gaps 46 therebetween, which extend proximally along a portion of the sleeve 42 and extend radially through to the passage 48 (FIG. 3), thereby allowing the fins 44 to be expanded radially.

The locking member 40 is slidably received over the cable 20 by orienting the fins 44 towards the spreader member 30, inserting the proximal end 24 of the cable 20 into the passage 48, and directing the locking member 40 distally. Generally, the passage 48 has a diameter substantially smaller than the base 36 of the spreader member 30, and preferably only slightly larger than the diameter of the cable 20. The spreader member 30 thereby substantially retains the locking member 40 on the cable 20. More preferably, the diameter of the passage 48 is only slightly larger than the diameter of the proximal end 35 of the spreader member 30. The cable 20 may be directed proximally in relation to the locking member 40, thereby forcing the inner surface 45 of the fins 44 to engage the tapered proximal surface 34 of the spreader member 30 and expanding the fins 44 radially outward as the spreader member 30 partially enters the passage 48.

The bone fixation device 10 (in FIG. 1) also includes a capturing assembly 60 for receiving the proximal end 24 of the cable 20 therethrough, and preferably for securing a proximal portion thereof. Preferably, the capturing assembly 60 includes a cooperating capturing sleeve 62 and threaded member 80. The capturing sleeve 62 has a substantially cylindrical portion 64 having a contractible cable passage 66 extending axially therethrough. The cable passage 66 preferably has an initial diameter slightly larger than the diameter of the cable 20, thereby allowing the cable 20 to be directed therethrough. The capturing sleeve 62 also has a raised portion 68 extending radially from an outer surface 65 of the cylindrical portion 64. Preferably, the raised portion 68 is an annular shaped flange integrally formed around the cylindrical portion 64, and including a distal or abutting surface 70.

Extending partially into the proximal end 72 of the cylindrical portion 64, is a substantially annular-shaped aperture 74 for receiving the threaded member 80 therein. The aperture 74 preferably has a threaded outer wall 76 and a substantially smooth inner wall 77, and has a gradually tapering cross-section as it extends distally into the cylindrical portion 64. The capturing sleeve 62 thus includes an annular-shaped flange 78 between the cable passage 66 and the aperture 74. Alternatively, the cylindrical portion 64 may include one or more flanges 78 disposed radially about the cable passage 66 and separated by slots or gaps (not shown) extending radially between the cable passage 64 and the aperture 74.

The threaded member 80 has a substantially annular crosssection similar to the aperture 74, although preferably slightly larger in cross-section than the aperture 74, and preferably has a threaded outer wall 82 and a substantially smooth inner wall 83 adapted to engage respectively the outer wall 76 and inner wall 77 of the capturing sleeve 62. The threaded member 80 preferably includes a hexagonal recess 86 in the proximal end 84 thereof for receiving a hexagonal nut driver (not shown), although alternatively, any suitable geometric recess or protrusion (not 5 shown) may be provided on the proximal end 84 for cooperating with a tool (not shown) to rotate the threaded member 80 in relation to the capturing sleeve 62. Thus, the threaded member 80 may be rotated about its longitudinal axis, thereby directing the threaded member 80 axially in relation to the capturing 10 sleeve 62 as the threaded walls 76 and 82 rotatably engage one another.

Preferably, the inner walls 77 and 83 are inclined as shown, such that they slidably engage one another as the threaded member 80 is rotated. Thus, as the threaded member 80 is directed 15 distally into the aperture 74, the flange 78 is forced radially inward, thereby contracting the cable passage 66. As should be appreciated by those skilled in the art, the capturing assembly 60 may include other socket or collect arrangements for reducing or contracting the diameter of the cable passage 66 to secure and 20 lock the cable 20 therein.

Figure 3:
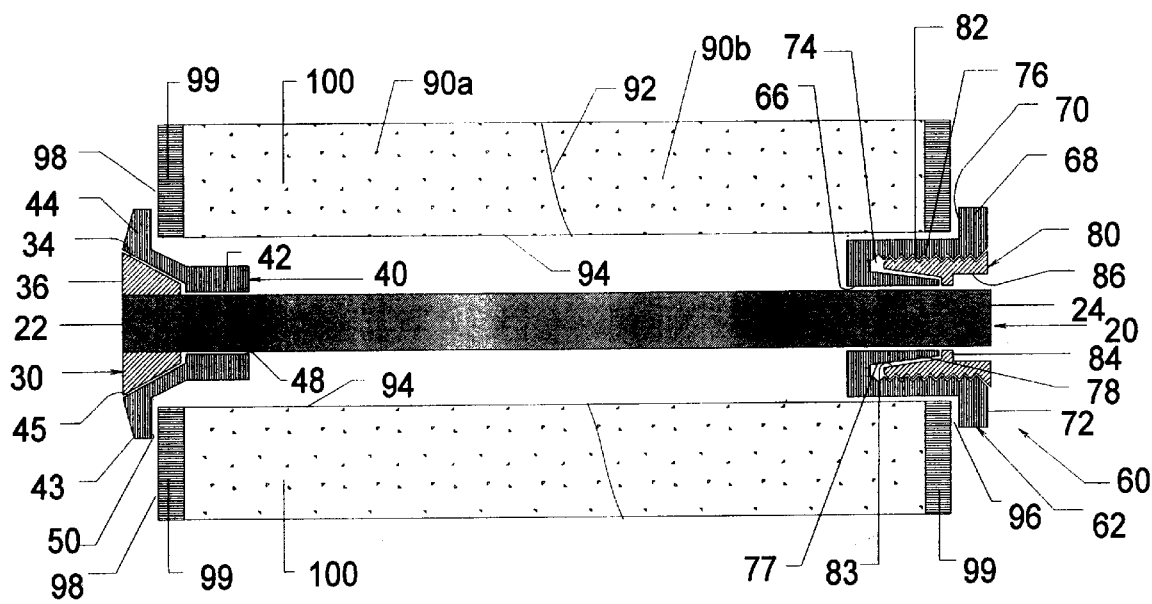
FIG. 3 is a cross-sectional view of the locking device of FIG. 1 engaging a bone structure having a fracture therein.
Figure 5A:
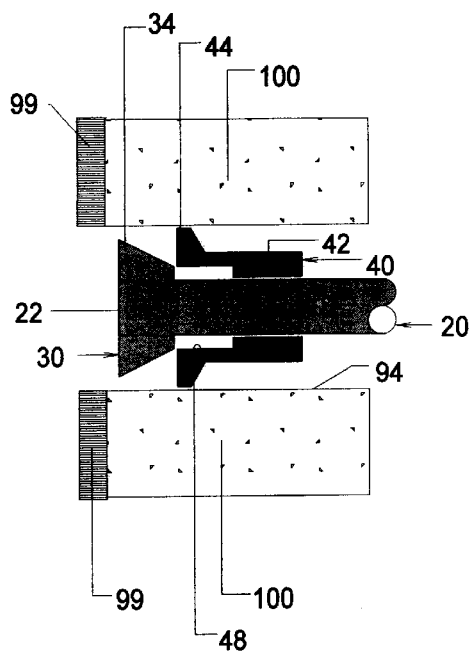
FIGS. 5A and 5B are cross-sectional views of the distal portion of the locking device of FIG. 1, showing the device in its contracted and enlarged conditions respectively.
Figure 5B:
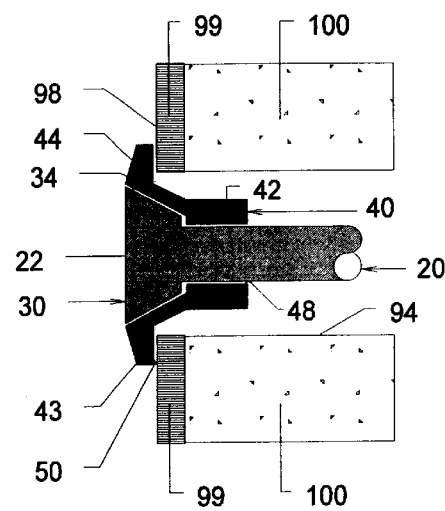

With particular reference to FIGS. 3, 5A and 5B, the locking device 10 may be implanted to fix bone fragments, preferably using the following steps. A bone 90 having a fracture 92 extending therethrough is positioned, such that the fragments 90a, 90b are oriented in a desired position for fixation. A hole 94 is drilled through the bone 90, preferably substantially perpendicular to the fracture 92, and/or substantially perpendicular to the outer surfaces of the bone 90, for example from an anterior surface 96 of the bone 90. The hole 94 preferably has a diameter slightly larger than the diameters of the fins 44 in their contracted condition and of the cylindrical portion 64, thereby allowing the bone fixation device 10 to be introduced therethrough (see FIG. 5A).

The distal end 22 of the cable 20, and the locking member 40 with the fins 44 in their contracted condition, are inserted into the hole 94 from the proximal or anterior surface 96, and directed distally until they partially emerge from the distal or posterior surface 98 of the bone 90. The fins 44 are expanded into their enlarged condition by tensioning the cable 20, that is, by directing the cable 20 proximally in relation to the locking member 40, causing the inner surface 45 of the fins 44 to engage the proximal surface 34 of the spreader member 30, and thereby forcing the fins 44 radially outward as the spreader member 30 partially enters the passage 48 within the locking member 40 (see FIG. 5B). With the fins 44 expanded, the proximal surface 50 of the locking member 40 may then abut or engage the posterior surface 98 of the bone 90.

The capturing assembly 60 may then be directed over the cable 20 to abut or engage the anterior surface 96 of the bone 90 adjacent the hole 94. Preferably, the proximal end 24 of the cable 20 is inserted through the cable passage 66 of the capturing sleeve 62, and the cylindrical portion 64 is directed into the hole 94 until the distal surface 70 of the capturing sleeve 62 substantially engages the anterior surface 96. The threaded member 80 is then directed over the cable 20 and into the aperture 74, or alternatively, may be loosely attached to the capturing sleeve 62 prior to introducing the capturing sleeve 62 over the cable 20.

While maintaining a predetermined tension on the proximal end 24 of the cable 20, the threaded member 80 is rotated, directing it distally into the aperture 74, thereby forcing the flange 78 radially inward and deformationally and/or frictionally engaging the cable 20. The tension may then be released from the proximal end 24 of the cable 20, thereby subjecting the bone fragments 90a, 90b to compressive forces as the cable 20 tends to pull the locking member 40 and the capturing sleeve 62 toward one another.

An important feature of the bone fixation device 10 in accordance with the present invention is that the compressive forces imposed by the cable 20 cause the proximal surface 50 of the locking member 40 and the distal surface 70 of the capturing member 62 to respectively engage the posterior surface 98 and the anterior surface 96 of the bone 90. These surfaces 96, 98 comprise cortical bone 99 which is substantially stronger than the cancellous bone 100 therebetween, and consequently the bone fixation device 10 provides improved fixation with substantially reduced likelihood of failure as compared to conventional implantation devices which rely on contact with cancellous bone 100 to fix the fragments 90a, 90b in their proper position.

In an alternative embodiment, an elongate substantially rigid rod (not shown) may be provided instead of the cable, the rod having threads extending at least partially along a proximal portion thereof. A retaining or spreader member may be provided on its distal end, and a locking member may be directed over the rod. The rod may be inserted into a hole drilled through a bone structure, as described above, whereupon the locking member may be directed distally to expand the fins into their enlarged condition as they engage the spreader member. A threaded member may then be screwed onto the proximal end of the rod, the threaded member having a raised portion to engage the anterior surface of the bone being stabilized. As the threaded member is tightened, the bone is substantially compressed between the fins on the locking member and the raised portion on the threaded member, thereby providing fixation of the fragments therebetween.

In a further alternative, the fins on the locking member may include substantially sharp or pointed edges and/or may be angled or curved in a proximal direction. The locking device may then be used to fix bone fragments without drilling completely through the bone being stabilized. A hole may be drilled across a fracture, the hole not extending completely through to the distal or far surface of the bone. The locking device may then be inserted into the hole to a predetermined depth beyond the location of the fracture being secured. The fins may be expanded similar to the method described above. However, instead of expanding to abut the posterior surface, the fins may engage or penetrate into the cancellous bone, thereby substantially anchoring the locking member in place.

A capturing assembly similar to that described above may then be directed onto the cable, the cable may be subjected to a predetermined tension, and the capturing assembly may be tightened to secure the cable therein. Thus, the bone may be held in compression between the fins engaging the cancellous bone within the hole and the capturing assembly engaging the anterior surface of the bone, thereby providing fixation of the fragments without penetrating the posterior surface of the bone.

In another alternative embodiment, the fins on the locking member and the raised portion on the capturing member may be provided in orientations not substantially perpendicular to the longitudinal axis of the cable, that is, the fins and/or the raised portion may define a plane that is not substantially perpendicular to the longitudinal axis of the cable. Such an embodiment may be useful for stabilizing bones when a hole is drilled through the bone that is not substantially perpendicular to the anterior and/or posterior surfaces of the bone, that is, the hole defines a predetermined angle with one or both surfaces. A locking device having fins and/or a raised portion defining a plane substantially matching the predetermined angle may be selected for implantation. Thus, when the locking device is implanted through the hole, the fins and/or raised portion may provide substantially improved engagement with the respective surfaces of the bone being stabilized.

Figure 4:
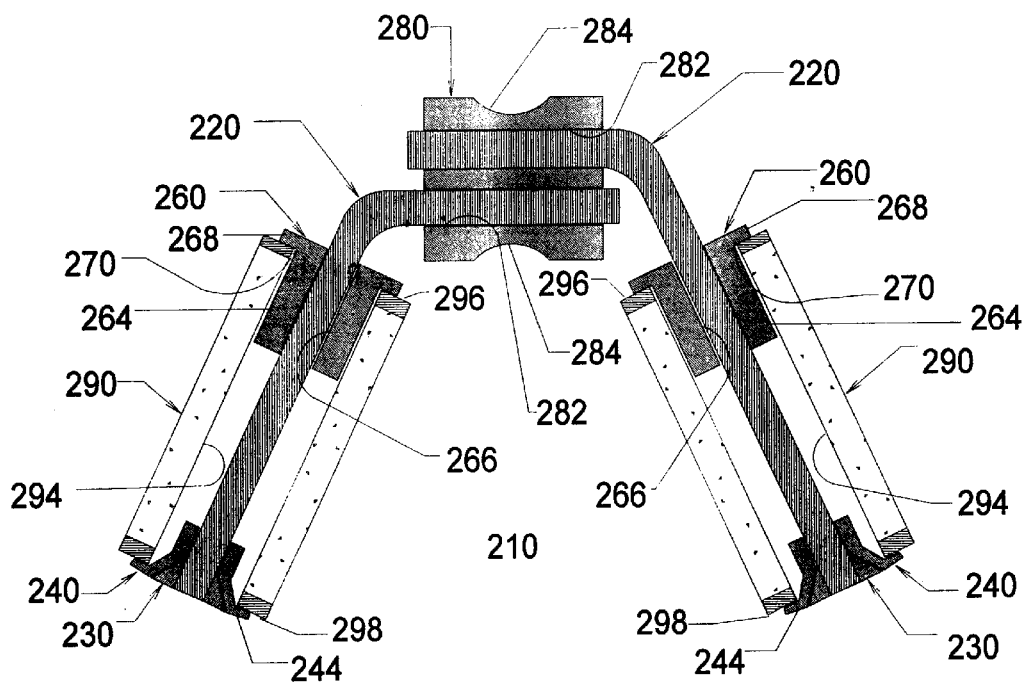
FIG. 4 is cross-sectional view of a second preferred embodiment of a locking device in accordance with the present invention engaging a pair of bone structures.

Turning now to FIG. 4, a second preferred embodiment of a locking device 210 is shown. The locking device 210 includes a pair of cables 220, spreader members 230, and locking members 240 similar to those described previously. The device 210 also includes a pair of centering sleeves 260. Each centering sleeve 260 includes a substantially cylindrical portion 264 having a cable passage 266 extending axially therethrough, the cable passage 266 having a diameter slightly larger than the diameter of the cable 220. The centering sleeve 260 also has a raised or abutting portion 268 extending radially from the cylindrical portion 264. Preferably, the raised portion 268 is annular shaped, is integrally formed around the cylindrical portion 264, and includes a distal surface 270.

In addition, the device 210 includes a crimper member 280, preferably formed from a substantially malleable metal or similar material. The crimper member 280 includes a pair of passages 282 extending therethrough, preferably being substantially parallel to one another and having initial diameters slightly larger than the diameters of the cables 220. Further, the crimper member 280 preferably has a substantially rectangular shape, and preferably includes recessed or weakened regions 284, adjacent the passages 282.

The locking device 210 is preferably used when two cables 220 are needed to stabilize separate bone fragments 290 with a fracture or to secure a dislocation between bone structures that requires fixation. For example, the locking device 210 may be particularly useful for stabilizing a displaced symphysis pubis.

Similar to the preferred embodiment described above, each cable 220 and locking member 240 is inserted into a respective hole 294 drilled into each bone 290, and the fins 44 are expanded to engage the respective posterior surface 298. A centering sleeve 260 is then directed over each cable 220 until they substantially engage the respective anterior surface 296, thereby preventing the cables 220 from abrading or otherwise damaging the bone adjacent the holes 294.

The cables 220 are then drawn through the holes 282 in the crimping member 280, preferably in opposite directions, as shown in FIG. 4, to substantially center the crimper member 280 and to transmit evenly the forces of the tensioned cables 220. The cables 220 are then tensioned by pulling them in opposite directions by a cable gripping tool (not shown. This opposes the bone fragments 290. Once a predetermined tension is applied to the cables 220, the crimper member 280 is compressed or crushed, preferably by crimping across the weakened regions 284, thereby securing the cables 220 within the crimper member 280, and stabilizing the bones 290.

The various components of the locking devices described herein may be provided from a variety of conventional materials suitable for surgical implants. For example, the cable or other elongate member may be fabricated from high strength metal alloys, such as 316L stainless steel, cobalt/chromium/molybdenum alloy, or Ti6AL4V alloy. The spreader member may be formed from metal, plastic or other suitable materials, and preferably 316L stainless steel, cobalt/chromium/molybdenum alloy, or Ti6AL4V alloy suitable to be substantially permanently attached to the cable, that allow the locking member to slide partially over the spreader member to expand the fins, and that have substantial strength to retain the locking member. The locking member may be formed from a substantially rigid material, such as 316L stainless steel, cobalt/chromium/molybdenum alloy, or Ti6AL4V alloy that may deform to expand the fins, yet substantially maintain its rigidity once the locking device is implanted within a bone structure. For example, the fins may include a notch or weakened region at their base to facilitate their expansion, yet be provided from a substantially rigid material capable of withstanding substantial tensile forces, preferably 316L stainless steel, cobalt/chromium/molybdenum alloy, or Ti6AL4V alloy. Similarly, the capturing assembly components ( i.e., the capturing sleeve, the threaded member, and the centering sleeve) may be formed from suitable metals, such as 316L stainless steel, cobalt/chromium/molybdenum alloy, or Ti6AL4V alloy. The crimper member preferably comprises a malleable metal, such as 316L stainless steel, cobalt/chromium/molybdenum alloy, or Ti6AL4V alloy. Other biologic polymers and biometals are on the forefront of development and could conceivably replace the above materials as suitable alternatives.

Figure 6:
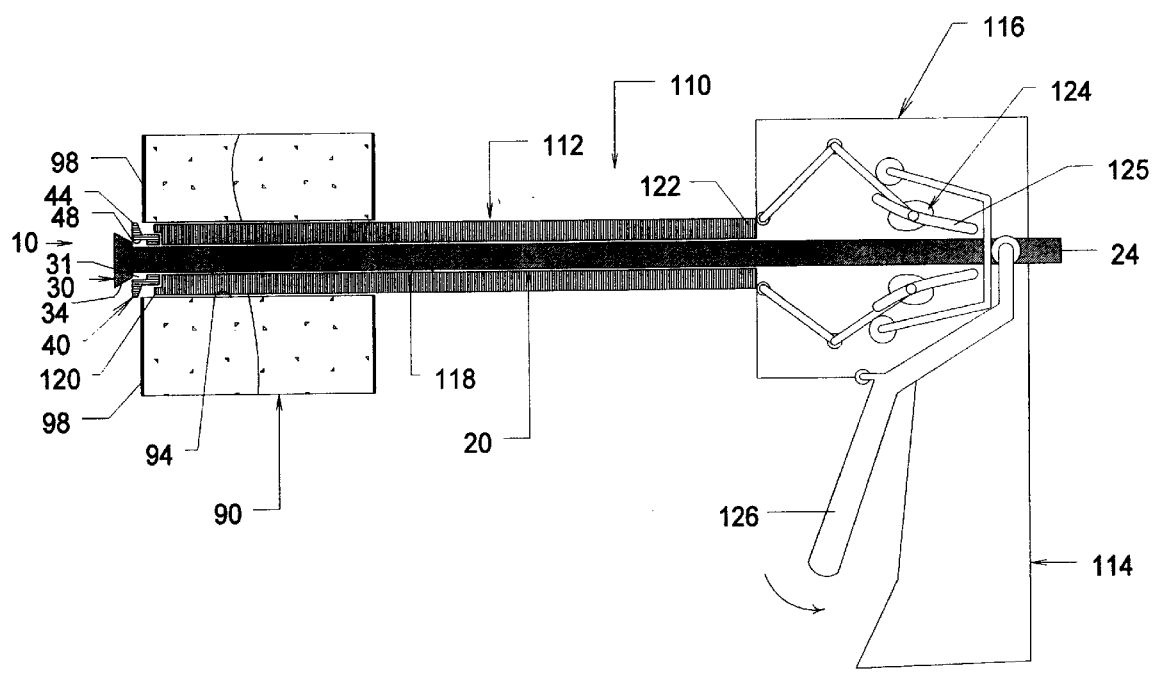
FIG. 6 is a cross-sectional view of an expanding tool for delivering and expanding a locking device in accordance with the present invention.
Figure 7:
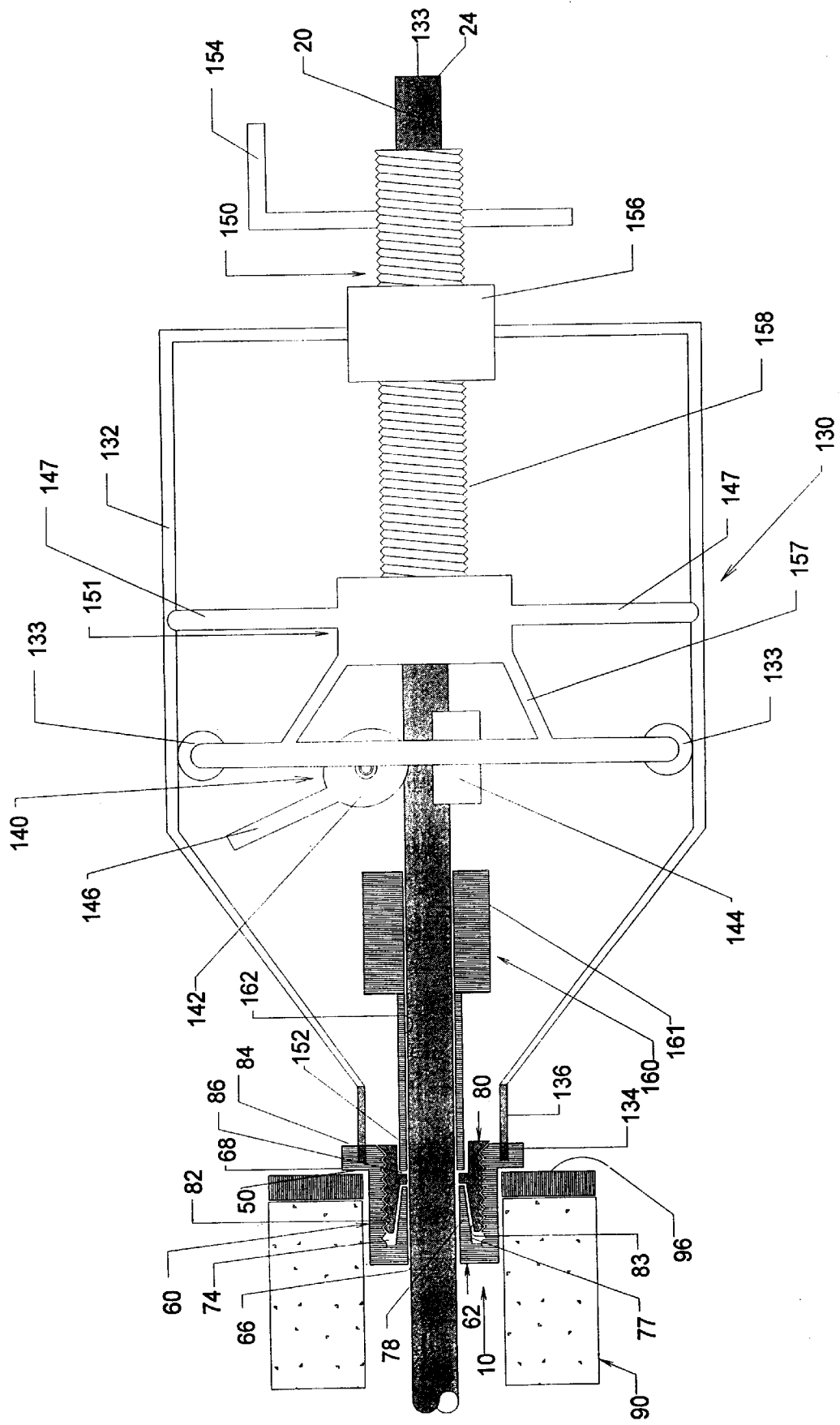
FIG. 7 is a cross-sectional view of a tightening tool for securely fixing a locking device in accordance with the present invention to a bone structure.

Another aspect of the present invention includes a number of tools that may be provided to assist in the implantation process. For example, as shown in FIG. 6, an expanding tool 110 may be provided to expand the fins 44 of the locking member 40 from their contracted condition to their enlarged condition (see FIGS. 5A and 5B). The tool 110 comprises an elongate tubular member 112, a handle 114, and a tensioning device 116. The tubular member 112 preferably has a passage 118 extending therethrough for receiving the cable 20, and may include protrusions, gripping fingers, or a similar mechanism (not shown) on its distal end 120 for holding the locking member 40 during introduction and expansion.

The proximal end 122 of the tubular member 112 is integrally formed on or attached to the handle 114, which provides a frame for supporting the tensioning device 116, and has a chamber 123 therein for receiving the cable 20 therethrough. The tensioning device 116 includespartially within saidember 124 at least partially within said chamber 123, and a trigger 126. The gripping member 124 mechanically and/or frictionally holds the cable 20 that is received through the tubular member 112 and/or applies a proximal, i.e. tensile force to the cable 20. With each pull of the trigger 126, the cable 20 is pulled a predetermined distance proximally and/or is subjected to an additional tensile force, the gripping member 124 maintaining the tension applied to the cable 20, as will be appreciated by those skilled in the art.

To use the tool 110, a locking device 10 is attached to the distal end 120 by inserting the proximal end 24 of the cable 20 through the tubular member 112 and into close continuity with the gripping member 116. The cable 20 may then be drawn proximally by pulling the proximal end 24 through the tubular member 112 until the locking member 40 abuts the distal end 120 of the tubular member 112 but does not expand the locking member 40.

The distal end 120 of the tool 110 with the locking device thereon is introduced into a hole 94 drilled through the bone structure 90 being stabilized. The tubular member 112 may include length graduations (not shown) extending from its distal end 120 for assisting a surgeon performing the implantation to insert the locking device 10 completely through the hole 94 to the posterior side 98 of the bone 90 (or optionally a predetermined distance past a fracture being secured). The trigger 126 may then be pulled as many times as appropriate to draw the cable 20 proximally. As the cable 20 is pulled, the spreader member 30 engages the fins 44, expanding the fins 44 radially outward as the spreader member 30 partially enters a passage 31 within the locking member 40. Once the fins 44 are fully expanded to their enlarged condition, the gripping member 124 may be released by releasing the handle 126, and the cable 20 removed from the tool 110.

Turning to FIG, 7, a tightening or locking tool 130 in accordance with the present invention may then be utilized to attach the capturing assembly 60 and complete the implantation of the locking device 10. The tool 130 includes a cable gripper member 140 and a rotating driver 150 attached to a frame or body 132, preferably disposed along a longitudinal axis 133 of the body 132, possibly including a handle or support structure (not shown). The distal end 134 of the tool 130 has longitudinal splines 136 for detachably receiving the proximal end 84 of the capturing sleeve 62, preferably preventing undesired rotational movement thereof. Alternatively, the distal end 134 may include a plurality of gripping prongs, or similar mechanical gripping mechanism (not shown).

The cable gripping member 140 allows mechanical security of the cable to longitudinal forces in the axis of the cable 133 by securing the cable against a roughened platform 144.

The cable gripper member 140 and the platform member 144 are linked to a trolley mechanism 151. The trolley mechanism 151 is mounted to the frame or body 132 via wheels 133 which roll the framework and by gliding anti-rotational plates 147 which prevent rotation of the trolley mechanism 151 during rotation of the rotating driver 150. The cable gripper 140 includes a handle 146 for loosening the traction on the cable 20 following tensioning. It also comprises a cam shaped metallic element 142 with roughened boarder for direct gripping of the cable 20 and is set in such a way that pulling on the cable 20 from the proximal end 24 by the trolley mechanism 151 only further tightens the mechanical interference against the cable 20. The rotational driver 150 is comprised of a treaded member for rotationally engaging a fixed threaded bolt member 156. It further contains a crank handle 154 for manually rotating the rotational driver 150. The rotational driver 150 is linked to the trolley mechanism 151 via a rotatable linkage (not shown) which allows the rotational driver 150 to apply axial traction to the trolley mechanism 151 in the axis 133 of the cable 20 while not causing a significant rotational moment on the trolley mechanism 151 being stabilized by the gliding antirotational plates 147.

The tightening tool 130 also is to be utilized with a cannulated hexagonal nut driver 160. This tool contains a passage 162 for the slidable containment of the cable 20 and a hexagonal distal end 152 for introduction into hexagonal recess 86 in the proximal end of the threaded member 80. The cannulated hexagonal nut driver also contains an expanded hexagonal shaped proximal end 161 for the adaption of typical box end wrench.

Use of the tightening tool 130 begins with the passage of the proximal end 24 of the cable 20 (already attached distally to the locking device 10) through the distal end of the capturing sleeve 62. The proximal cable 24 may then be threaded through the distal end of the threaded member and the distal end of the cannulated hexagonal nut driver 152 respectively. The cable is then fed through the cable gripping member 140 and through the rotatable driver 150. The cable 20 may then be gripped along its proximal end 24 by one's hand and pulled through the tightening tool 130 until the longitudinal splines 130 make solid contact into the holes (not shown) in the proximal end 84 of the collar 68 on the capturing sleeve 62. The distal aspect 50 of the collar 68 should then come to rest against the proximal cortex of the bone 96. The handle 154 may then be turned so as to shorten the distance between the trolley mechanism 151 and the bolt member 156. The attached cable 20 would thus be drawn proximally through the passage 66 in the capturing sleeve 62 which is held at length by the longitudinal splines 136. When a predetermined tension in the cable had been obtained, the capturing sleeve 62 would be secured to the cable 20 by insertion of the threaded member 80. This would be done by using a box end wrench to turn the cannulated hexagonal nut driver so as to rotatably insert the distal end of the threaded member 80 into the annular space in the capturing sleeve 74. This would cause the flanges 78 to press securely against the cable 20 securing the implant. The cable 20 could then be released from tightening tool 130 by lifting the handle 146 and releasing the cam shaped metallic element 142 from the cable 20. The cable could then be withdrawn and sheared off to the length desired using a standard cable cutting device.

A tightening tool (not shown) similar to that described above may also be provided to facilitate implantation of a locking device including a pair of cables and a crimper member. The tool may include a pair of pulleys for turning the cables and directing them in opposite directions across a pair of cable tensioners. Preferably, the tool also includes a crimping mechanism for receiving the crimper member disposed between and in line with the cable tensioners. The cables may be directed through the crimper member and a predetermined tension applied using the cable tensioners. The crimping mechanism may then crush the crimper member, thereby securing the cables and substantially locking the bones being stabilized in position.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A locking device for compressibly securing a tissue structure, said locking device comprising:
   an elongate member, having proximal and distal ends, and having a proximal portion;
   a locking member slidably received on said elongate member, and having a radially expandable portion, said radially expandable portion including a proximal surface for engaging a far or distal surface of a tissue structure;
   a retaining member on the distal end of said elongate member, said retaining member being adapted to slidably engage said locking member thereby preventing said locking member from sliding distally beyond said elongate member; and
   a capturing assembly having a contractible passage therethrough for securably receiving said proximal portion of said elongated member, said capturing assembly including a raised portion having a distal surface for engaging a near or proximal surface of the tissue structure.

2. The locking device of claim 1, wherein said radially expandable portion of said locking member comprises a plurality of fins disposed radially about said locking member, said plurality of fins including said proximal surface for engaging the far or distal surface of the tissue structure.

3. The locking device of claim 1, wherein:
   said retaining member includes a tapered portion extending proximally along said elongate member;
   said locking member includes an expandable passage therein, said expandable passage being at least partially defined by said radially expandable portion; and
   said radially expandable portion is adapted to be expanded when said tapered proximal portion slidably engages said expandable passage.

4. The locking device of claim 1, wherein said capturing assembly comprises:
   a capturing sleeve having a proximal end, having a substantially annular-shaped aperture therein extending distally from said proximal end, and having a flange at least partially defining said contractible passage;
   an annular-shaped member adapted to be received in said aperture, and being axially adjustable within said aperture; and
   wherein said flange at least partially contracts said contractible passage when said annular-shaped member is directed distally within said aperture.

5. The locking device of claim 1, wherein said elongate member comprises a cable.

6. The locking device of claim 1, wherein said tissue structure comprises a bone having a fracture located between said proximal or near and distal or far surfaces.

7. An orthopaedic implant device for compressibly stabilizing a bone structure having a fracture therein, said implant device comprising:
   an elongate member, having proximal and distal ends, and having a proximal portion;
   a spreader member attached to the distal end of said elongate member, said spreader member having a tapered portion extending proximally from said distal end of said elongate member;
   a locking member slidably received on said elongate member, and having a radially expandable portion, said expandable portion being expandable between a contracted condition and an enlarged condition when said locking member slidably engages said tapered portion of said spreader member; and
   a capturing assembly having a contractible passage therethrough for securably receiving said proximal portion of said elongate member, said capturing assembly including a raised portion extending radially therefrom.

8. The implant device of claim 7, wherein said radially expandable portion comprises a plurality of fins disposed radially about said locking member, said plurality of fins including a proximal surface for engaging a posterior surface of a bone structure being compressed by said implant device when said fins are expanded to said enlarged condition.

9. The implant device of claim 7, wherein said capturing assembly comprises:
   a capturing sleeve having a proximal end, having a substantially annular-shaped aperture therein extending distally from said proximal end, and having a flange at least partially defining a wall of said contractible passage;
   an annular-shaped member adapted to be received in said aperture, and being axially adjustable within said aperture; and
   wherein said flange at least partially contracts said contractible passage when said annular-shaped member is directed distally within said aperture.

10. The implant device of claim 9, wherein said raised portion comprises an annular-shaped flange disposed radially about said capturing sleeve, said annular-shaped flange having a distal surface for engaging an anterior surface of a bone structure being compressed by said implant device.

11. The implant device of claim 9, wherein said flange at least partially defines a wall of said aperture, and wherein said annular-shaped member forces said flange radially inward when said annular-shaped member is directed distally within said aperture.

12. The implant device of claim 9, wherein said annular-shaped member comprises a first threaded surface, and said aperture comprises a second threaded surface adapted to cooperate with said first threaded surface, whereby said annular-shaped member is directed axially when said threaded surfaces rotatably engage one another.

13. The implant device of claim 7, wherein said capturing assembly comprises:
   a centering sleeve having a passage extending axially therethrough for receiving said elongate member therethrough, and having said raised portion thereon; and
   a crimper member formed from a substantially malleable material, and having said contractible passage extending therethrough for securably receiving said proximal portion of said elongate member.

14. The implant device of claim 13, wherein said raised portion comprises an annular-shaped flange disposed radially about said centering sleeve, said annular-shaped flange having a distal surface for engaging an anterior surface of a bone structure being compressed by said implant device.

15. The implant device of claim 13, further comprising:

a second elongate member having a second spreader member attached thereon, having a second locking member slidably received thereon, and having a second centering member for receiving said elongate member therethrough; and wherein said crimper member comprises a second contractible passage extending therethrough for securably receiving a proximal portion of said second elongate member.

16. The implant device of claim 7, wherein said elongate member comprises a cable.

* * * * *

UNITED STATES PATENT AND TRADEMARK OFFICE
CERTIFICATE OF CORRECTION

PATENT NO. : 5,919,194
DATED : July 6, 1999
INVENTOR(S) : David L. Anderson

Page 1 of 1

It is certified that error appears in the above-identified patent and that said Letters Patent is hereby corrected as shown below:

Column 2,
Line 17, please change "tensionresistance" to -- tension-resistance --.

Column 4,
Line 22, please change "SA and SB" to -- 5A and 5B --.

Column 5,
Line 6, please change "proximal end 35" to -- proximal end 24 --.
Line 50, please delete "5".
Line 56, please delete "10".
Line 61, please delete "15".
Line 66, please delete "20".

Column 8,
Line 17, please change "(not shown" to -- (not shown) --.

Column 9,
Line 15, please change "chamber 123" to -- chamber 118 --.
Lines 16 and 17, please change "includespartially within saidember" to -- includes a movable gripping member --.

Column 10,
Line 37, please change "driver 152" to -- driver 160 --.
Line 42, please change "splines 130" to -- splines 136 --.
Line 46, please change "bone 96" to -- bone 90 --.

Signed and Sealed this

Twenty-eighth Day of August, 2001

*Attest:*

*Attesting Officer*

NICHOLAS P. GODICI
*Acting Director of the United States Patent and Trademark Office*